United States Patent
Marinos

(10) Patent No.: US 11,452,885 B2
(45) Date of Patent: Sep. 27, 2022

(54) WATER TANK APPARATUS

(71) Applicant: Elekta Limited, Crawley (GB)

(72) Inventor: Nikolas Marinos, West Sussex (GB)

(73) Assignee: Elekta Limited, Crawley (GB)

( * ) Notice: Subject to any disclaimer, the term of this patent is extended or adjusted under 35 U.S.C. 154(b) by 0 days.

(21) Appl. No.: 15/733,493

(22) PCT Filed: Feb. 19, 2019

(86) PCT No.: PCT/GB2019/050431
§ 371 (c)(1),
(2) Date: Aug. 11, 2020

(87) PCT Pub. No.: WO2019/158947
PCT Pub. Date: Aug. 22, 2019

(65) Prior Publication Data
US 2021/0101025 A1 Apr. 8, 2021

(30) Foreign Application Priority Data
Feb. 19, 2018 (GB) ...................................... 1802641

(51) Int. Cl.
*A61N 5/10* (2006.01)
(52) U.S. Cl.
CPC .... *A61N 5/1075* (2013.01); *A61N 2005/1076* (2013.01)
(58) Field of Classification Search
CPC ...................... A61N 5/1075; A61N 2005/1076
See application file for complete search history.

(56) References Cited

U.S. PATENT DOCUMENTS

| | | | |
|---|---|---|---|
| 5,635,709 A * | 6/1997 | Sliski | G01T 1/169 250/252.1 |
| 6,207,952 B1 * | 3/2001 | Kan | A61N 5/1048 250/252.1 |
| 7,193,220 B1 * | 3/2007 | Navarro | G01T 1/169 250/252.1 |

(Continued)

FOREIGN PATENT DOCUMENTS

| | | |
|---|---|---|
| CN | 201765330 U | 3/2011 |
| CN | 102265182 A | 11/2011 |

(Continued)

OTHER PUBLICATIONS

"International Application Serial No. PCT GB2019 050431, International Preliminary Report on Patentability dated Sep. 3, 2020", 8 pgs.

(Continued)

*Primary Examiner* — Blake C Riddick
(74) *Attorney, Agent, or Firm* — Schwegman Lundberg & Woessner, P.A.

(57) ABSTRACT

A water tank apparatus for use with a radiotherapy system, comprising a base, side walls, end walls, and a top wall, together defining a tank structure, wherein an aperture is defined in the top wall near one end wall, and an upstanding rim surrounding the aperture; and a sensor mounting body fixed within the tank structure, and having formations by which a radiation sensor can be located in a fixed position within the tank structure so as to detect radiation at a point equidistant from the side wall and top wall and base.

14 Claims, 5 Drawing Sheets

(56) References Cited

U.S. PATENT DOCUMENTS

| | | | |
|---|---|---|---|
| 2008/0048125 A1* | 2/2008 | Navarro | A61N 5/1075 250/389 |
| 2009/0200476 A1* | 8/2009 | Brusasco | A61N 5/1048 250/370.07 |
| 2010/0019137 A1 | 1/2010 | Torre et al. | |
| 2010/0119033 A1 | 5/2010 | Li et al. | |
| 2010/0176284 A1* | 7/2010 | Navarro | A61N 5/1075 250/252.1 |
| 2010/0243875 A1 | 9/2010 | Plompen et al. | |
| 2011/0022360 A1* | 1/2011 | Simon | A61N 5/10 702/189 |
| 2011/0278444 A1* | 11/2011 | Navarro | G01T 1/169 250/252.1 |
| 2014/0263990 A1* | 9/2014 | Kawrykow | A61N 5/1031 250/252.1 |
| 2015/0071408 A1* | 3/2015 | Ebstein | A61N 5/1075 378/65 |
| 2015/0090892 A1* | 4/2015 | Matsushita | G01T 1/02 250/389 |
| 2015/0306427 A1* | 10/2015 | Hirasawa | G01T 1/204 250/363.08 |
| 2015/0343241 A1* | 12/2015 | Han | A61N 5/1075 378/205 |
| 2015/0360056 A1 | 12/2015 | Xing et al. | |
| 2016/0135765 A1* | 5/2016 | Vigdor | G01T 1/169 250/366 |
| 2018/0250526 A1* | 9/2018 | McCoy | A61N 5/1048 |
| 2018/0311513 A1* | 11/2018 | Sakamoto | A61N 5/1031 |
| 2018/0318609 A1* | 11/2018 | Arican | A61N 5/1075 |
| 2020/0061391 A1* | 2/2020 | Krishnaswamy | A61N 5/10 |
| 2020/0346041 A1* | 11/2020 | Krishnaswamy | A61B 5/7292 |

FOREIGN PATENT DOCUMENTS

| | | | |
|---|---|---|---|
| CN | 104865590 A | | 8/2015 |
| CN | 106861058 A | | 6/2017 |
| EP | 1852714 A1 | | 11/2007 |
| EP | 2148222 A1 | | 1/2010 |
| EP | 2857865 A1 | | 4/2015 |
| FR | 2723212 | | 2/1996 |
| GB | 201618326 | | 12/2016 |
| JP | 2002360715 A | | 12/2002 |
| JP | 2003047666 | | 2/2003 |
| JP | 2003047666 A | * | 2/2003 |
| JP | 2004129678 A | | 4/2004 |
| JP | 2010044057 A | | 2/2010 |
| JP | 2011133467 A | | 7/2011 |
| JP | 2013190436 A | | 9/2013 |
| WO | WO-2014120423 A1 | | 8/2014 |
| WO | WO-2019158947 A1 | | 8/2019 |

OTHER PUBLICATIONS

"International Application Serial No. PCT/GB2019/050431, International Search Report dated Jun. 6, 2019", 5 pgs.

"International Application Serial No. PCT/GB2019/050431, Written Opinion dated Jun. 6, 2019", 6 pgs.

"United Kingdom Application Serial No. 1802641.9, Office Action dated Jul. 27, 2018", 4 pgs.

Martin, Nielsen S, et al., "Validating PET segmentation of thoracic lesions—is 4D Pet necessary?", Biomedical Physics & Engineering Express, vol. 3, No. 1, (Feb. 16, 2017), 9 pgs.

"Chinese Application Serial No. 201980014297.8, Office Action dated Jul. 5, 2022", w/English Translation, (Jul. 5, 2022), 12 pgs.

* cited by examiner

WATER TANK APPARATUS

PRIORITY APPLICATIONS

This application is a U.S. National Stage Filing under 35 U.S.C. § 371 from International Application No. PCT/GB2019/050431, filed on Feb. 19, 2019, and published as WO2019/158947 on Aug. 22, 2019, which claims the benefit of priority to United Kingdom Application No. 1802641.9, filed on Feb. 19, 2018; the benefit of priority of each of which is hereby claimed herein, and which applications and publication are hereby incorporated herein by reference in their entirety.

FIELD OF THE INVENTION

The present invention relates to a water tank apparatus suitable for use in making calibration measurements in a radiotherapy system. The invention also extends to methods of using such a tank and to making measurements.

BACKGROUND ART

Image guided radiotherapy (IGRT) uses imaging of a patient and close control of a radiotherapy system to provide controlled and targeted doses of radiation, such as x-rays, to treat tumours. Magnetic resonance imaging (MRI) has been proposed as the imaging system. Because of the technical requirements in an MRI system, the patient must be positioned in a bore of relatively limited dimensions through which the radiation beam is projected. While frequent calibration of the radiotherapy system is useful for accurate control, the limited dimensions of the bore make this difficult.

It has been proposed to make radiation measurements in a water tank to better understand the output of a radiation source. JP 2004 129678 discloses a water phantom device for IMRT (intensity modulated radiotherapy) measurement that is provided with a water tank which has a tank body part filled with water and extended horizontally and an inlet part which communicates with the tank body part with a fluid and has the upper end thereof extended vertically above the uppermost part of the tank body part. A sensor is arranged in the tank body part to measure a radiation dose irradiated and a positioning means for positioning the sensor at a desired point within the body tank part, is further provided. The positioning means is located outside the tank.

If routine calibration is to be performed, it is useful if the system can be easily and quickly set up and struck down in a relatively short time so as to interfere with the use of the system as little as possible. The present invention intends to address such issues as measurement of the radiation output, particularly in a system including an MRI guidance system.

SUMMARY OF THE INVENTION

One aspect of the invention provides a water tank apparatus for use with a radiotherapy system, comprising a base, side walls, end walls, and a top wall, together defining a tank structure, wherein an aperture is defined in the top wall near one end wall, and an upstanding rim surrounding the aperture; and a sensor mounting body fixed within the tank structure, and having formations by which a radiation sensor can be located in a fixed position within the tank structure so as to detect radiation at a point equidistant from the side wall and top wall and base.

The sensor mounting body can comprise a wall extending from the base and including one or more apertures by which the radiation sensor is mounted in the fixed position.

The base, side walls, end walls, and top wall can have substantially constant thickness.

One or more polymer blocks can be provided for location on top of the top wall. The polymer block can include one or more polymers and other materials such that the behaviour of the block in the radiation beam substantially matches that of water, i.e. "solid water".

The apparatus can further comprise a mounting plate by which the tank structure can be mounted on a patient bearing couch of a radiotherapy system. The mounting plate can include structures that are engageable in indexing formations on the couch so as to retain the tank structure in a predetermined position on the couch.

The apparatus can further comprise a radiation sensor connected to the sensor mounting body. The radiation sensor can be a dosimeter such as a sensor including a Farmer chamber.

The point at which the radiation sensor detects radiation can be spaced from the sensor mounting body and an end wall such that, when the apparatus is placed in the radiation beam of a radiotherapy system, the periphery of the radiation field produced by the radiation beam that includes the point is spaced from the sensor mounting body, end wall, side walls, base, and top wall.

Another aspect of the invention provides a method of detecting radiation from a radiotherapy system, comprising connecting a dosimeter sensor to the sensor mounting body of the apparatus; filling the tank structure with water to a level within the upstanding rim that is higher than the top wall; positioning the apparatus in the radiotherapy system such that the radiation detection point is substantially at the isocentre of the radiation beam of the radiotherapy system; measuring the radiation with the beam directed through the top wall and base; and measuring the radiation with the beam directed through the side walls.

The method can comprise measuring radiation with the direction of radiation direction being from the top wall to the base, from a first side wall to a second side wall, from the base to the top wall, and from the second side wall to the first side wall. With the detection point lying on an axis extending between the end walls, this can correspond to positioning the source at 0°, 90°, 180°, and 270° positions around this axis.

The method can further comprise placing a polymer block on the top wall, and measuring radiation with the beam directed through the polymer block, the top wall, and the detection point (e.g. with the source at the 0° position). Alternatively, the polymer block can be placed adjacent one of the side walls, and a radiation measurement made with the beam directed in the corresponding direction (e.g. with the source and the 90° or 270° position).

Further aspects of the invention will be apparent from the following description.

BRIEF DESCRIPTION OF THE DRAWINGS

The invention will now be described by way of example and with reference to the accompanying figures in which.

DETAILED DESCRIPTION OF THE EMBODIMENTS

Figure 1:
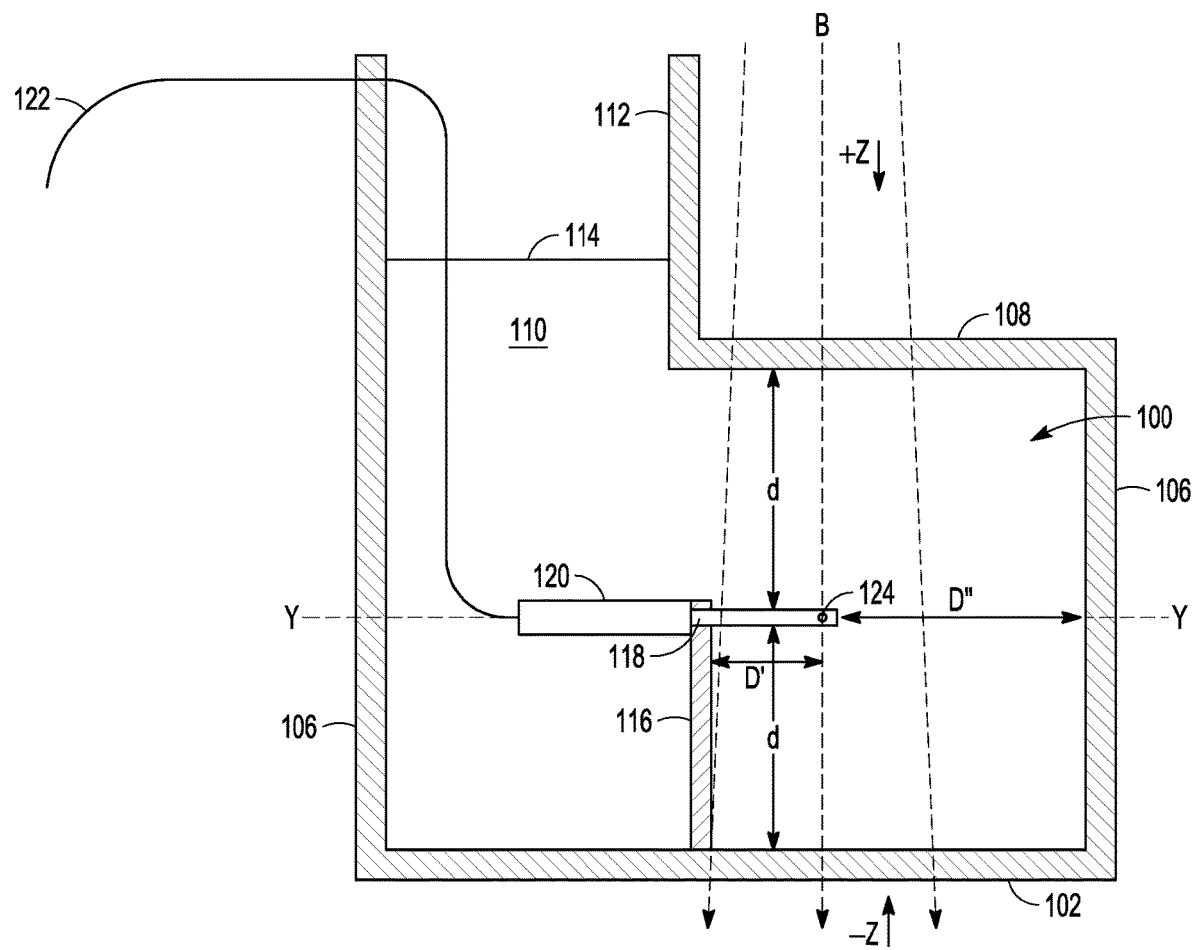
FIG. 1 shows a schematic side view of a water tank apparatus.
Figure 2:
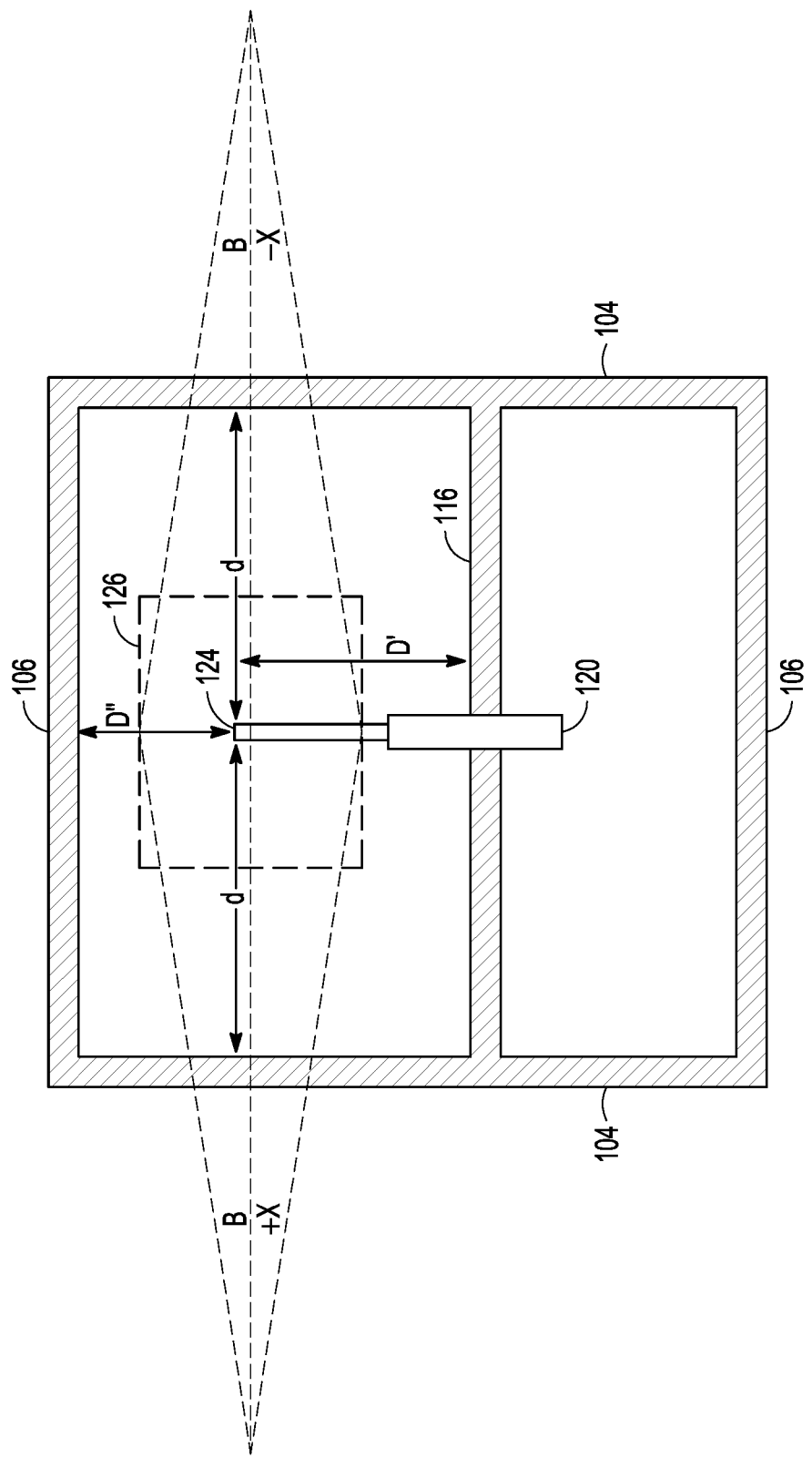
FIG. 2 shows a schematic top view of the water tank apparatus of FIG. 1.

FIGS. 1 and 2 show views of a water tank apparatus. Neither view is to scale, nor are relative proportions indicated. The apparatus comprises a water tank 100 having walls defined by a base plate 102, side plates 104, end plates 106, and a top plate 108. An aperture 11 is defined in the tope plate 108 adjacent one end plate 106, the aperture 110 being surrounded by an upstanding rim 112. The rim 112 can be formed from upward extensions of the end plate 106, the side plates 102, and the top plate 108. The base plate 102, side plates 104, end plates 106, and top plate 108 can be of constant thickness and materials, for example an acrylic glass such as 1.5 cm Perspex (PMMA).

The aperture 110 and rim 112 mean that the tank 100 can be filled with water to a level 114 that lies above the top plate 108, thus ensuring that the volume of the tank below the tope plate 108 is completely full.

A support wall 116 is provided within the tank 110 extending up from the base plate 102 so as to define a sensor mounting body. Apertures 118 are defined in the support wall 116 by which a radiation sensor 120 can be located within the tank 100. The radiation sensor can comprise a Farmer chamber and can be connected by a cable 122 to an electrometer (not shown) to provide a radiation dosimetry measurement.

The sensor 120 is mounted such that its measurement point 124 is in a predetermined position suitable for dosimetry measurement in a radiotherapy system. In the apparatus shown in FIGS. 1 and 2, the measurement point is located on a central axis Y-Y of the tank 100 extending between the end plates 106. The tank is dimensioned such that the measurement point 124 is equidistant (d) from the side walls 106, the base 102 and the top plate 108. Thus a radiation beam B entering the tank through the top plate 108, one or other of the side plates 102, or the base plate 102, will pass through the same amount of water to reach the measurement point 124.

The measurement is also spaced from the support wall 116, and from the end plate 106 by sufficient distance D', D", that a divergent beam B entering from any radial (X-X) position around the axis Y-Y does not intersect either the support wall 116 or end plate 106 before racing the measurement point 124. Distance D' and D" can be selected to allow a measurement volume 126 to be defined in the tank that includes the periphery of the beam B.

Figure 3:
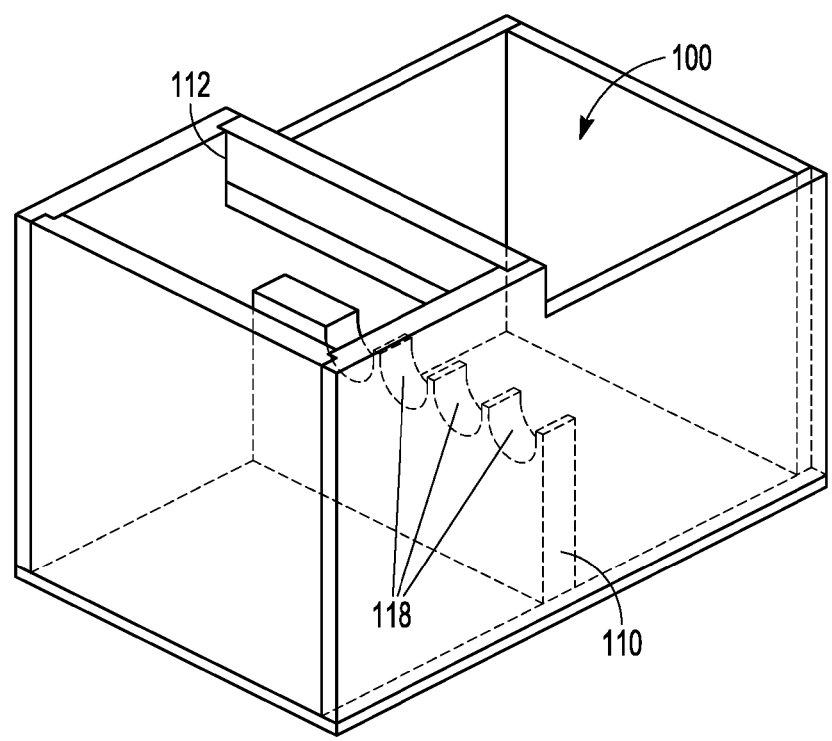
FIG. 3 shows a perspective view of a water tank apparatus of the type shown in FIGS. 1 and 2.

FIG. 3 shows a perspective view of the water tank 100. The support wall 118 includes a number of apertures or cut-outs 118 that allow the sensor 120 to be removably mounted in the tank 100, but to be held securely in place for measurement. The apertures can have a shape that allows the sensor to be inserted into its measurement location and held in place by any suitable securing means, such as locking rings and collars (not shown), and to be removed from the tank when the measurement is completed. Similarly, the dimensions of the aperture 110 and rim 112 are selected to allow insertion and removal of the sensor 120.

Figure 4:
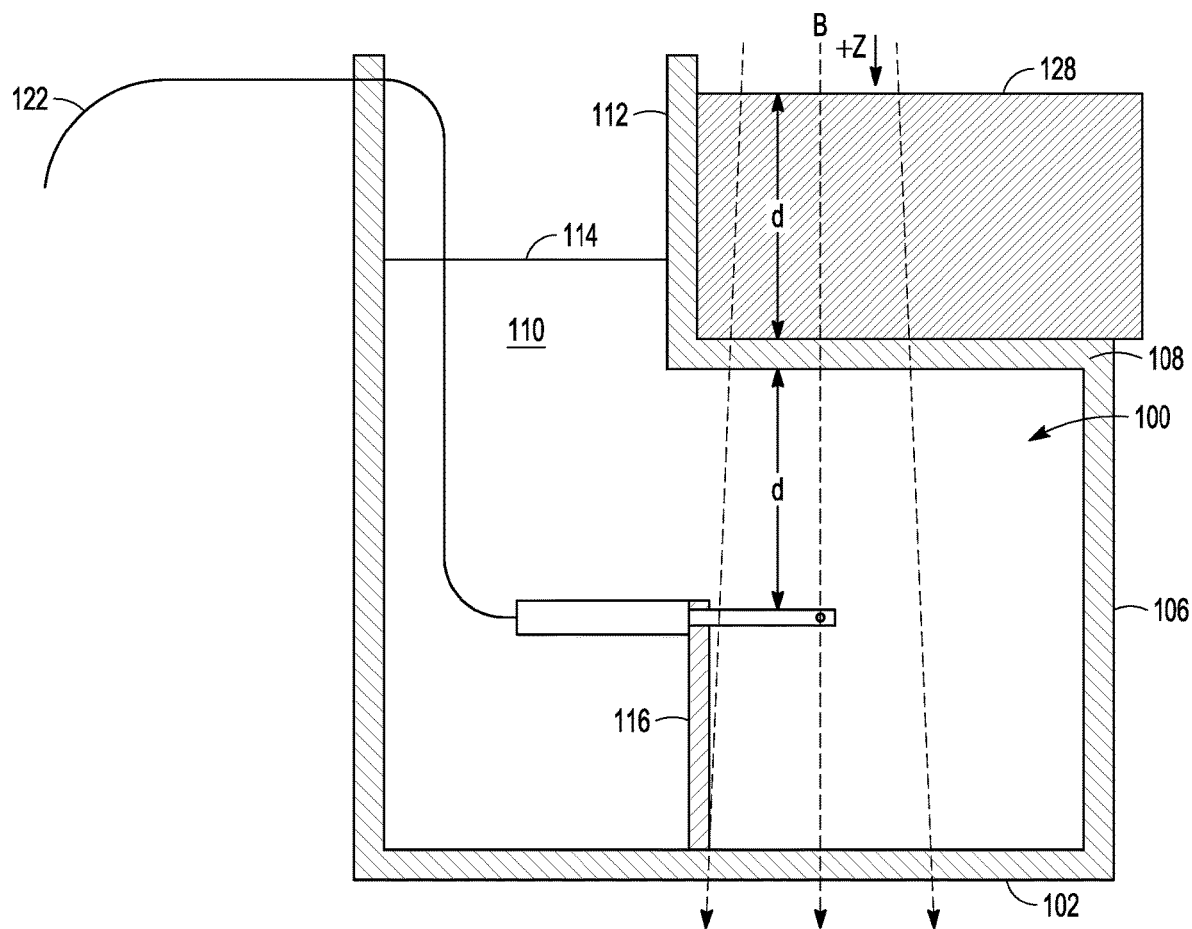
FIG. 4 shows a schematic side view of a water tank apparatus including a polymer block.

FIG. 4 shows a view comparable to that of FIG. 1, but further including a polymer block 128 positioned on the top plate 108. The polymer block is made from a polymer material that optionally includes additives, such that it attenuates an x-ray beam in substantially the same way as an equivalent volume of water. Such polymer materials are known as "solid water". The thickness d of the block 128 is comparable to the separation d of the measurement point from the top plate 108. Consequently, a measurement made with the block 128 in place and the beam direction +Z through the top plate 108 will have a water attenuation of essentially twice that of the corresponding measurement without the block 128 in place (FIG. 1). Comparing these two measurements can be useful in calibrating the sensor 120.

Figure 5:
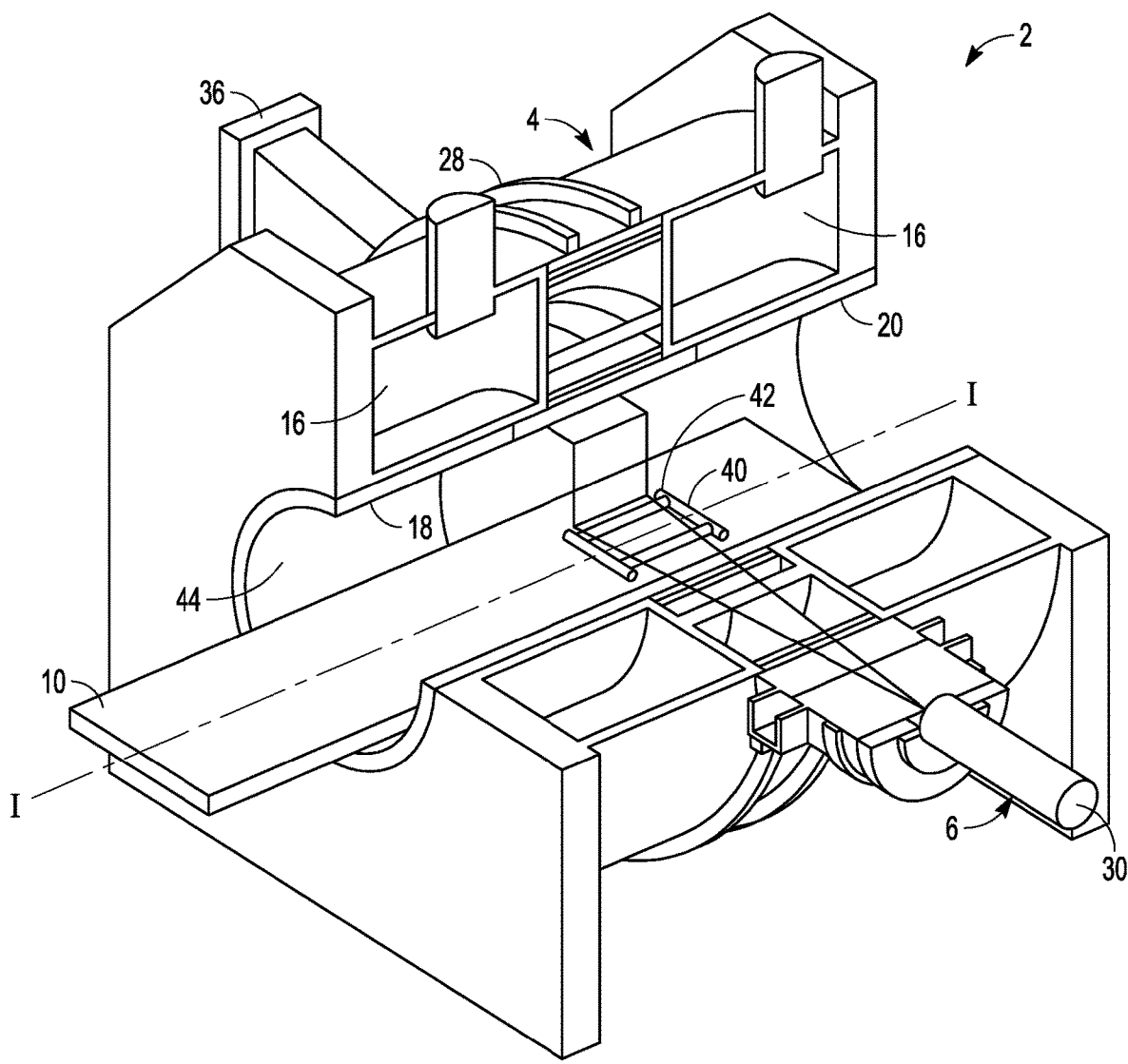
FIG. 5 shows a radiotherapy system.

FIG. 5 shows a system 2 comprising a radiotherapy apparatus 6 and a magnetic resonance imaging (MRI) apparatus 4.

The system includes a patient support or couch 10, for supporting a patient in the apparatus. The couch 10 is movable along a horizontal, translation axis (labelled "I"), such that a patient resting on the couch is moved into the radiotherapy and MRI apparatus as described in WO 2009/007737.

The system 2 also comprises an MRI apparatus 4, for producing real-time images of a patient positioned on the couch 10. The MRI apparatus includes a primary magnet 16 which acts to generate the primary magnetic field for magnetic resonance imaging. The magnetic field lines generated by the magnet 16 run substantially parallel to the central translation axis I. The primary magnet 16 comprises one or more coils with an axis that runs parallel to the translation axis I. The one or more coils may be a single coil or a plurality of coaxial coils of different diameter, as illustrated. The coil(s) in the primary magnet 16 is arranged such that a central window of the magnet 16 is free of coils. The magnet 16 may further comprise one or more active shielding coils, for generating a magnetic field outside the magnet 16 of approximately equal magnitude and opposite polarity to the primary magnetic field. The more sensitive parts of the system 2, such as the accelerator, are positioned in this region outside the magnet 16 where the magnetic field is cancelled, at least to a first order. The MRI apparatus 4 further comprises two gradient coils 18, 20, which generate the gradient magnetic field that is superposed on the primary magnetic field. These coils 18, 20 generate a gradient in the resultant magnetic field that allows spatial encoding of the protons so that their position can be determined from the frequency at which resonance occurs (the Larmor frequency). The gradient coils 18, 20 are positioned around a common central axis with the primary magnet 16, and are displaced from one another along that central axis. This displacement creates a gap, or window, between the two coils 18, 20. In an embodiment where the primary magnet 16 also comprises a central window between coils, the two windows are aligned with one another.

An RF system transmits radio signals at varying frequencies towards the patient, and detects the absorption at those frequencies so that the presence and location of protons in the patient can be determined. The RF system may include a single coil that both transmits the radio signals and receives the reflected signals, dedicated transmitting and receiving coils, or multi-element phased array coils, for example. Control circuitry (not shown) controls the operation of the various coils 16, 18, 20 and the RF system, and signal-processing circuitry receives the output of the RF system, for generating images of the patient supported by the couch 10.

The system 2 further comprises a radiotherapy system 6 which delivers doses of radiation to a patient supported by the couch 10. The majority of the radiotherapy apparatus 6, including at least a radiation beam generator 30 (e.g. an x-ray source) is mounted on a gantry or chassis 28. The gantry 28 is an annular structure having a bore into which the couch 10 can extend, and is continuously rotatable around the couch 10 when it is inserted into the treatment area, powered by one or more gantry/chassis motors. A radiation detector (not shown) is also mounted on the gantry 28 opposite the radiation beam generator 30 and with the rotational axis of the gantry positioned between them. The gantry 28 is arranged such that it can be rotated through more than 360 degrees in any direction, a slip ring being provided to allow power to be provided to the components mounted on the gantry 28.

A mounting plate 40 is provided which has formations that engage in indexing formations 42 on the couch 10. The mounting plate 409 is configured to hold the tank 100 in position. The tank 44 is dimensioned so that it can fit in the bore 44 of the MRI system 4. By mounting the tank 44 on the couch 10 and advancing the couch such that the tank 100 sits within the bore 44, the measurement point 124 can be placed at the isocentre of the beam B produced by the generator 30.

With the tank positioned in the bore in this way, a series of measurement can be made to allow calibration of the generator 30 so that control of the beam can be effected for optimum radiotherapy treatments. For effective calibration, it is useful to make a series of measurements, with the generator in different radial positions around the tank. For example, a series of four measurements can be taken: with the generator positioned vertically above the top plate 108 (+Z, 0°), horizontally through a first side plate 104 (+X, 90°), vertically below the base plate 102 (−Z, 180°), and horizontally through the other side plate 104 (−X, 270°). In each position, the beam B will pass through the same distanced in the water-filled tank 100, and therefore can provide a comparable indication of the dose received at the isocentre 124 when irradiated from each direction.

The sensor 120 can be calibrated by making two measurements, one without the block 128, and one with. The variation between the two measurements will provide an indication of the variation of the sensor signal with beam path length through water and so allow the dose to be determined.

In use, the sensor 120 can be secured to the mounting wall 116, and the tank 100 can be secured to the couch 10. The tank can then be filled with water until the level 114 in the rim 112 is above the top plate 108, thus ensuring that the tank 100 is completely full. The couch can then be advanced to position the measurement point 124 at the isocentre, and the measurement taken with the source at different rotational positions. Calibration using the sold water block 128 can be performed before, during, or after these measurements. When the measurements are complete, the tank 100 can be withdrawn from the bore 44 and emptied of water, the sensor removed, and the tank and mounting plate 40 removed from the couch 10 leaving the system ready for use. Such a series of measurements can be made once per day, such as before the first use of the day, the measurements being provided to a control system for providing controlled doses of radiation to a patient on the couch.

Various changes can be made within the scope of the invention. For example, the tank described above has a square section around the measurement point, which allows the four measurements to be made. The exact section of the tank is not important as long as the equidistant positioning of the measurement point for the measurement directions can be maintained. The overall volume and external dimensions of the tank can vary according the size of the bore, or any other physical constraints of the system. The sensor can be any suitable sensor for the measurement to be made.

The invention claimed is:

1. A water tank apparatus for use with a radiotherapy system, comprising:
    a base, a first side wall and an opposing second side wall, a first end wall and an opposing second end wall, and a top wall, wherein the first end wall, the second end wall, the first side wall, and the second side wall extend between the base and the top wall to define a tank structure, wherein an aperture is defined in the top wall adjacent to at least one of the first end wall or the second end wall, and wherein an upstanding rim surrounds the aperture; and
    a sensor mounting body fixed within the tank structure configured to position a sensor measurement point of a radiation sensor at a predetermined fixed position within the tank structure that is located at a point equidistant from the first side wall, the second the side wall, the top wall, and the base to detect radiation.

2. The apparatus as claimed in claim 1, wherein the sensor mounting body comprises a wall extending from the base and including at least one aperture by which the radiation sensor is mounted in the fixed position.

3. The apparatus as claimed in claim 1, wherein the base, the first side wall, the second side wall, the first end wall, the second end wall, and the top wall have a constant thickness.

4. The apparatus as claimed in claim 1, further comprising at least one polymer block located on top of the top wall.

5. The apparatus as claimed in claim 1, further comprising a mounting plate configured to mount the tank structure to a patient bearing couch of a radiotherapy system.

6. The apparatus as claimed in claim 5, wherein the mounting plate includes a structure that is engageable in an indexing formation on the couch so as to retain the structure of the tank in an indexed position on the couch.

7. The apparatus as claimed in claim 1, further comprising the radiation sensor connected to the sensor mounting body.

8. The apparatus as claimed in claim 7, wherein the point at which the radiation sensor detects radiation is spaced from the sensor mounting body and at least one of the first end wall or the second an end wall such that, when the apparatus is placed in a radiation beam of a radiotherapy system, a periphery of a radiation field produced by the radiation beam that includes the point is spaced from the sensor mounting body, at least one of the first end wall or the second end wall, at least one of the first side wall or the second side wall, the base, and the top wall.

9. The apparatus as claimed in claim 7, wherein the radiation sensor is a dosimeter.

10. The apparatus as claimed in claim 9, wherein the dosimeter includes a Farmer chamber.

11. The apparatus as claimed in claim 1, further comprising at least one polymer block being located adjacent to at least one of the first side wall or the second side wall.

12. A method of detecting radiation from a radiotherapy system, comprising:
    connecting a dosimeter sensor to an apparatus, the apparatus including:
    a base, a first side wall, a second side wall, a first end wall, a second end wall, and a top wall, together defining a tank structure, wherein an aperture is defined in the top wall adjacent to at least one of the first end wall or the second end wall, and an upstanding rim surrounding the aperture; and
    a sensor mounting body fixed within the tank structure, the sensor mounting body configured to position a sensor measurement point of a radiation sensor, the radiation sensor located in a fixed position within the tank structure such that the sensor measurement point of the radiation sensor is located at a point equidistant from the first side wall, the second side wall, the top wall, and the base; and wherein the dosimeter sensor is connected to the sensor mounting body;

filling the tank structure with water to a level within the upstanding rim that is higher than the top wall;

positioning the apparatus in the radiotherapy system such that the radiation detection point is located at an isocentre of a radiation beam of the radiotherapy system;

measuring the radiation with the beam directed through the top wall and the base; and measuring the radiation with the beam directed through at least one of the first side wall or the second the side wall.

13. The method as claimed in claim 12, further comprising:

measuring radiation with a direction of radiation being from the top wall to the base, from the first side wall to the second side wall, from the base to the top wall, and from the second side wall to the first side wall.

14. The method as claimed in claim 12, further comprising:

placing a polymer block on at least one of, the top wall or adjacent to at least one of the first side wall or the second a side wall; and measuring radiation with the beam directed through the polymer block, the at least one of the top, the first side wall, or the second side wall, and the radiation detection point.

* * * * *

UNITED STATES PATENT AND TRADEMARK OFFICE
CERTIFICATE OF CORRECTION

PATENT NO. : 11,452,885 B2
APPLICATION NO. : 15/733493
DATED : September 27, 2022
INVENTOR(S) : Nikolas Marinos It is certified that error appears in the above-identified patent and that said Letters Patent is hereby corrected as shown below:

In the Claims

In Column 7, Line 6, in Claim 12, delete "base;" and insert --base,-- therefor

Signed and Sealed this
Thirteenth Day of December, 2022

Katherine Kelly Vidal
*Director of the United States Patent and Trademark Office*